United States Patent [19]

Kao et al.

[11] B 4,053,467

[45] Oct. 11, 1977

[54] PROSTAGLANDIN DERIVATIVES

[75] Inventors: Wenling Kao, Devon; Donald P. Strike, St. Davids, both of Pa.

[73] Assignee: American Home Products Corporation, New York, N.Y.

[21] Appl. No.: 491,711

[22] Filed: July 25, 1974

[44] Published under first Trial Voluntary Protest Program on Mar. 23, 1976

Related U.S. Application Data

[63] Continuation-in-part of Ser. No. 485,411, July 3, 1974, abandoned.

[51] Int. Cl.$^2$ .................................. C07L 177/00
[52] U.S. Cl. .......................... 542/426; 260/514 D; 560/121; 424/305; 424/317
[58] Field of Search ........... 260/468 D, 514 D, 240 R

[56] References Cited

U.S. PATENT DOCUMENTS

| | | | |
|---|---|---|---|
| 3,728,382 | 4/1973 | Bundy | 260/468 D |
| 3,804,889 | 4/1974 | Bundy | 260/514 D |
| 3,804,890 | 4/1974 | Bundy | 260/514 D |
| 3,812,172 | 5/1974 | Bundy | 260/514 D |
| 3,812,179 | 5/1974 | Bundy | 260/514 D |
| 3,845,042 | 10/1974 | Strike et al. | 260/240 R |

FOREIGN PATENTS DOCUMENTS

| | | | |
|---|---|---|---|
| 2,193,613 | 2/1974 | France | 260/468 |

OTHER PUBLICATIONS

Guzman et al., Chem. & Industry (London) 1973, pp. 635–636.
Grudzinskas et al., Tet. Letters, 1973, No. 2, pp. 141–144.
Vogel et al., Helvetia Chim. Acta 56 (1973), pp. 557–560.

*Primary Examiner*—Arthur P. Demers
*Attorney, Agent, or Firm*—Robert Wiser

[57] ABSTRACT

Prostaglandin compounds substituted at the 11-position with a methyl group are prepared from PGA$_2$, its 15-epimer, and their esters. These compounds, not heretofore found in nature, possess a variety of pharmacological activities one of which is bronchodilation.

12 Claims, 3 Drawing Figures

PROSTAGLANDIN DERIVATIVES

CROSS-REFERENCE

This application is a continuation-in-part of copending application Ser. No. 485,411, filed July 3, 1974 now abandoned.

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation, the ability to reduce gastric secretion, and to modify blood pressure.

The present invention concerns prostaglandin compounds in which the 11-position (using the prostanoic acid numbering system) is substituted with a methyl group. Several 11-methyl prostaglandin molecules have previously been synthetically prepared, see for example Belgian Patent No. 803,854; C. V. Grudzinskas, and M. J. Weiss, Tetrahedron Letters, 141 (1973); and A. Guzman, and P. Crabbe, Chemistry and Industry, 635 (1973).

SUMMARY OF THE INVENTION

The invention sought to be patented in a first composition aspect resides in the concept of a chemical compound of the structure

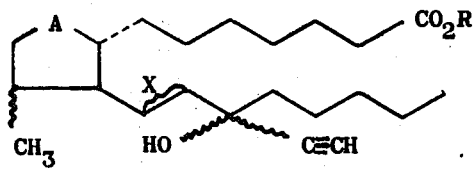

wherein A is CHOH or C=O; R is H or alkyl of from 1 to 6 carbon atoms, and
  i. X is a single bond; or
  ii. X is a trans double bond.

The tangible embodiments of the first composition aspect of the invention possess the inherent general physical properties of being clear to yellow oils, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the first composition aspect of the invention possess the inherent applied use characteristic of exerting gastric anti-secretory and hypotensive effects, and when A is C=O, bronchodilating effects, upon administration to warm-blooded animals. These effects are evidenced by pharmacological evaluation according to standard test procedures, and, in addition, are useful as intermediate in the synthesis of other compositions of the invention.

The invention sought to be patented in a second composition aspect resides in the concept of a chemical compound of the structure:

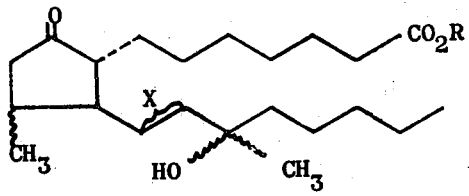

wherein R is H or alkyl of from 1 to 6 carbon atoms, and
  i. X is a single bond; or
  ii. X is a trans double bond.

The tangible embodiments of the second composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the second composition aspect of the invention possess the inherent applied use characteristic of exerting bronchodilating gastric anti-secretory and hypotensive effects upon administration to warm-blooded animals as evidenced by pharmacological evaluation according to standard test procedures, and, in addition, are useful as intermediates in the synthesis of other compositions of the invention.

The invention sought to be patented in a third composition aspect resides in the concept of a chemical compound of the structure

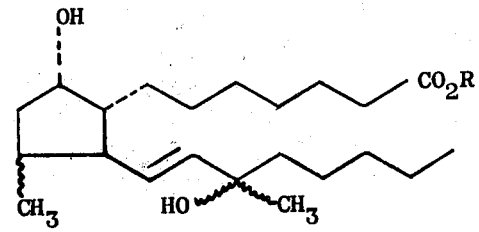

wherein R is H or alkyl of from 1 to 6 carbon atoms.

The tangible embodiments of the third composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the composition sought to be patented.

The tangible embodiments of the third composition aspect of the invention possess the inherent applied use characteristic of exerting gastric anti-secretory effects upon administration to warm-blooded animals as evidenced by pharmacological evaluation according to standard test procedures, and, in addition, are useful as intermediates in the synthesis of other compositions of the invention.

The invention sought to be patented in a fourth composition aspect resides in the concept of a chemical compound of the structure

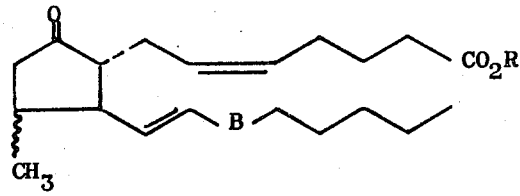

wherein B is $C(CH_3)OH$ or $C(C \equiv CH)OH$, and R is H or alkyl of from 1 to 6 carbon atoms.

The tangible embodiments of the fourth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the fourth composition aspect of the invention possess the inherent applied use characteristic of exerting bronchodilating, gastric anti-secretory and hypotensive effects upon administration to warm-blooded animals as evidenced by pharmacological evaluation according to standard test procedures, and, in addition, are useful as intermediates in the synthesis of other compositions of the invention.

The invention sought to be patented in a fifth composition aspect resides in the concept of a chemical compound of the structure

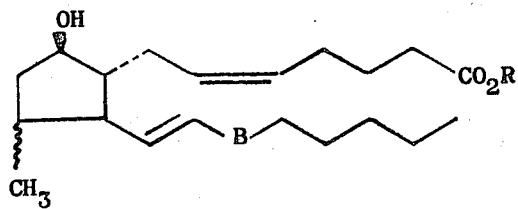

wherein B is $C(CH_3)OH$, or $C(C \equiv CH)OH$; and R is H, or alkyl of from 1 to 6 carbon atoms.

The tangible embodiments of the fifth composition aspect of the invention possess the inherent possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the fifth composition aspect of the invention possess the inherent applied use characteristic of exerting bronchodilating, effects upon administration to warm-blooded animals as evidenced by pharmacological evaluation according to standard test procedures, and, in addition, are useful as intermediates in the synthesis of other compositions of the invention.

The invention sought to be patented in a sixth composition aspect resides in the concept of a chemical compound of the structure

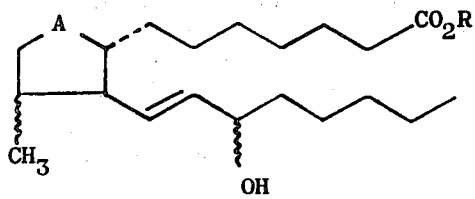

wherein A is CHOH or C=O; and R is H or alkyl of from 1 to 6 carbon atoms.

The tangible embodiments of the sixth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the composition sought to be patented.

The tangible embodiments of the sixth composition aspect of the invention possess the inherent applied use characteristic of exerting hypotensive effects upon administration to warm-blooded animals as evidenced by pharmacological evaluation according to standard test procedure, and, in addition, are useful as intermediates in the synthesis of other compositions of the invention.

The invention sought to be patented in a seventh composition aspect resides in the concept of a chemical compound of the structure

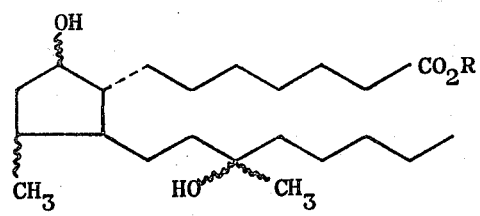

wherein R is H or alkyl of from 1 to 6 carbon atoms.

The tangible embodiments of the seventh composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the seventh composition aspect of the invention posses the inherent applied use characteristic of being intermediates in the synthesis of other compositions of the invention.

The invention sought to be patented in an eighth composition aspect resides in the concept of a chemical compound of the structure

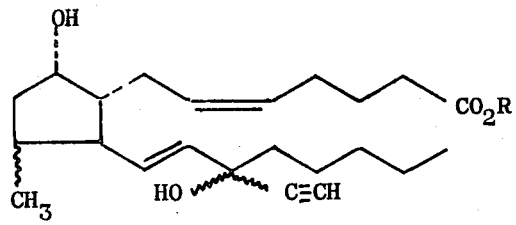

wherein R is H, or alkyl of from 1 to 6 carbon atoms.

The tangible embodiments of the eighth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the eighth composition aspect of the invention possess the inherent applied use characteristic of being intermediates in the synthesis of other compositions of the invention.

The invention sought to be patented in a ninth composition aspect resides in the concept of a chemical compound of the structure

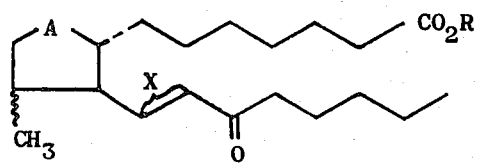

wherein A is CHOH or C=O; R is H or alkyl of from 1 to 6 carbon atoms, and
  i. X is a single bond; or
  ii. X is a trans double bond.

The tangible embodiments of the ninth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the ninth composition aspect of the invention possess the inherent applied use characteristic of being intermediates in the synthesis of other composition of the invention.

The invention sought to be patented in a tenth composition aspect resides in the concept of a chemical compound of the structure

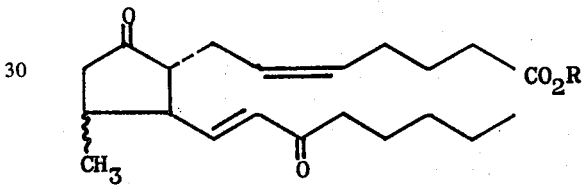

wherein R is H or alkyl of from 1 to 6 carbon atoms.

The tangible embodiments of the tenth composition aspect of the invention possess the inherent general physical properties of being either crystalline solids or clear to yellow oils, are substantially insoluble in water and are generally soluble in polar solvents such as ethyl acetate and ether. Examination of compounds, produced according to the hereinafter described process reveals, upon infrared, nuclear magnetic resonance, and mass spectrographic analysis, spectral data supporting the molecular structures wherein set forth. The aforementioned physical characteristics, taken together with the nature of the starting materials, the mode of synthesis, and the elemental analyses, confirm the structure of the compositions sought to be patented.

The tangible embodiments of the tenth composition aspect of the invention possess the inherent applied use characteristic of being intermediates in the synthesis of other compositions of the invention.

The invention sought to be patented in an eleventh composition aspect resides in the concept of a chemical compound of the structure

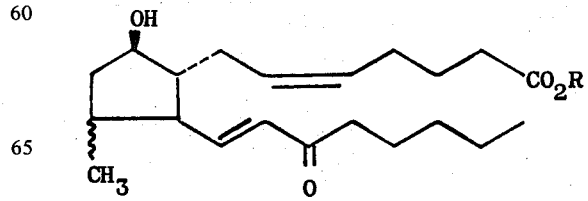

wherein R is H or alkyl of from 1 to 6 carbon atoms.

The tangible embodiments of the eleventh composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the eleventh composition aspect of the invention possess the inherent applied use characteristic of being intermediates in the synthesis of other compositions of the invention.

The invention sought to be patented in a twelfth composition aspect resides in the concept of a chemical compound of the structure

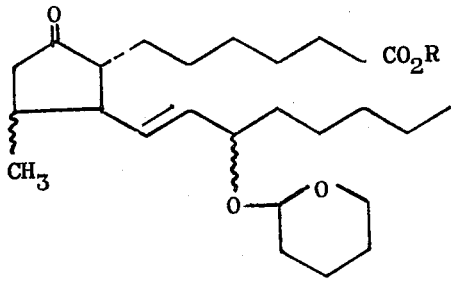

wherein R is H or alkyl of from 1 to 6 carbon atoms.

The tangible embodiments of the twelfth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the twelfth composition aspect of the invention possess the inherent applied use characteristic of being intermediates in the synthesis of other compositions of the invention.

The invention sought to be patented in a thirteenth composition aspect resides in the concept of a chemical compound of the structure

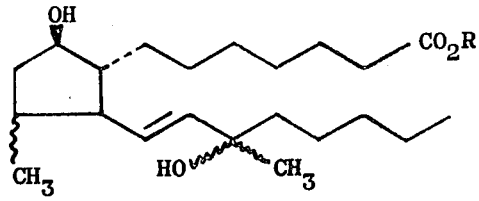

wherein R is H or alkyl of from 1 to 6 carbon atoms.

The tangible embodiments of the thirteenth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the thirteenth composition aspect of the invention possess the inherent applied use characteristic of being intermediates in the synthesis of other compositions of the invention.

DESCRIPTION OF THE PREFERRED EMBODIMENTS

Figure 1:
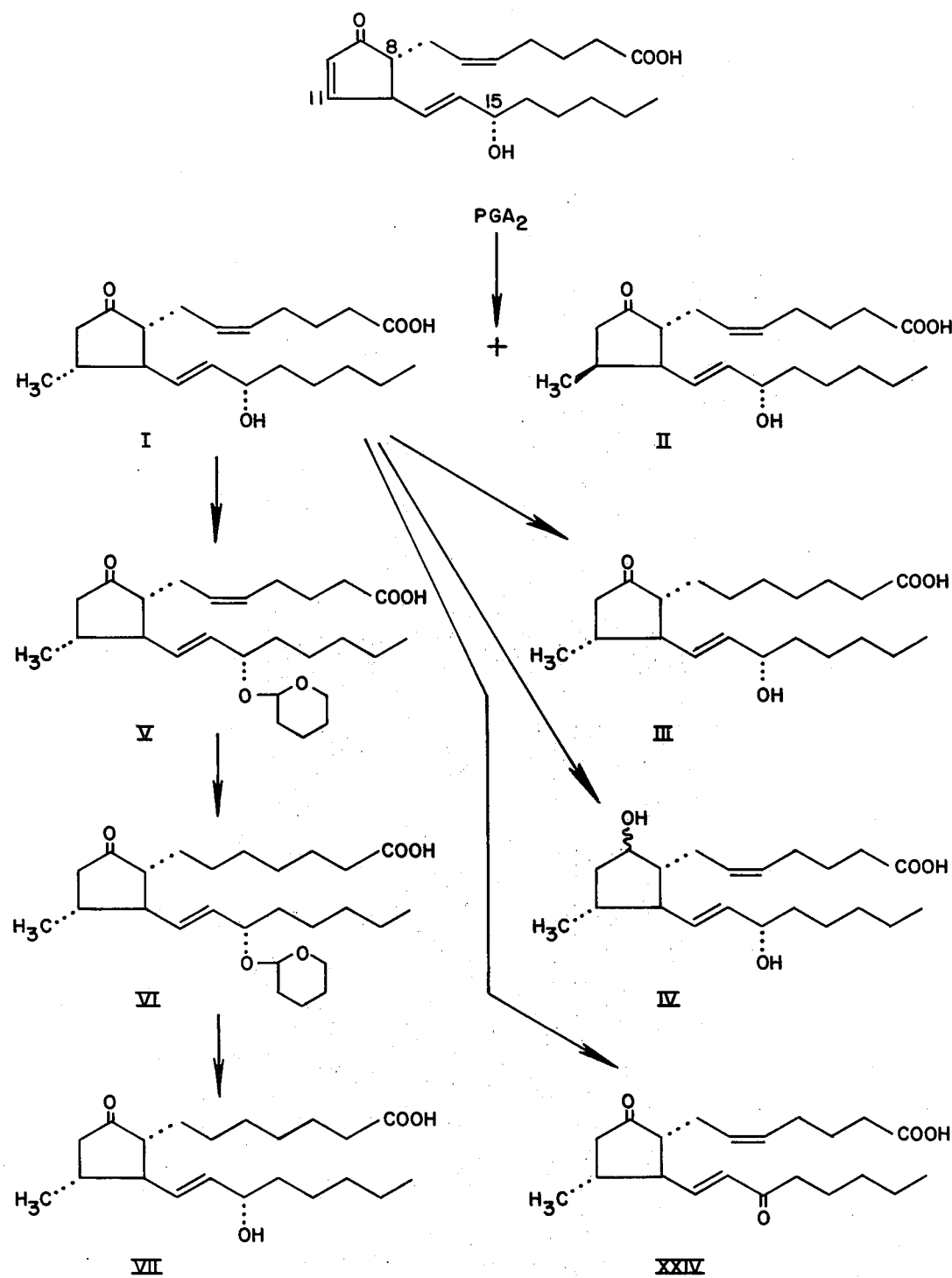
Figure 2:
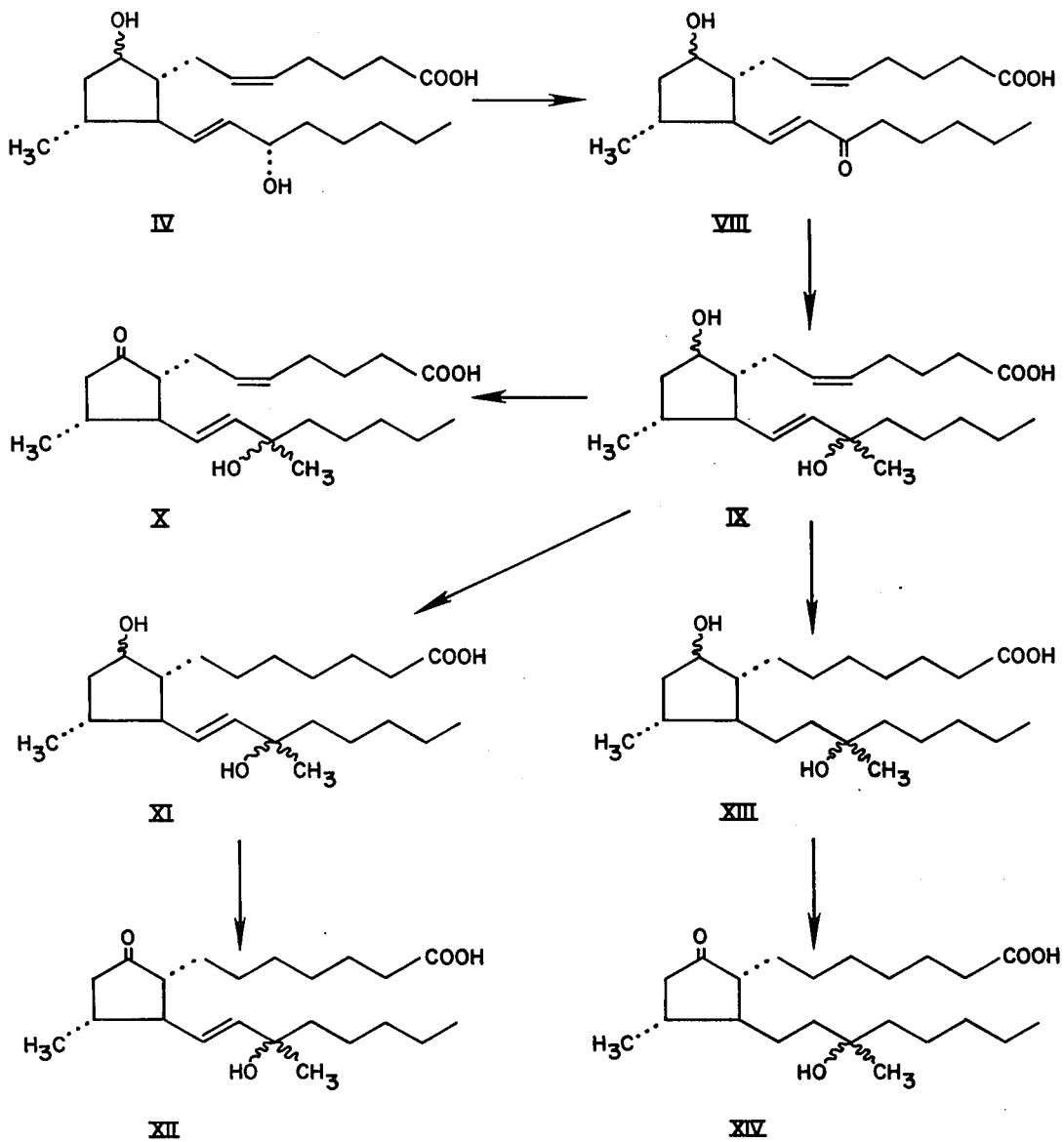
Figure 3:
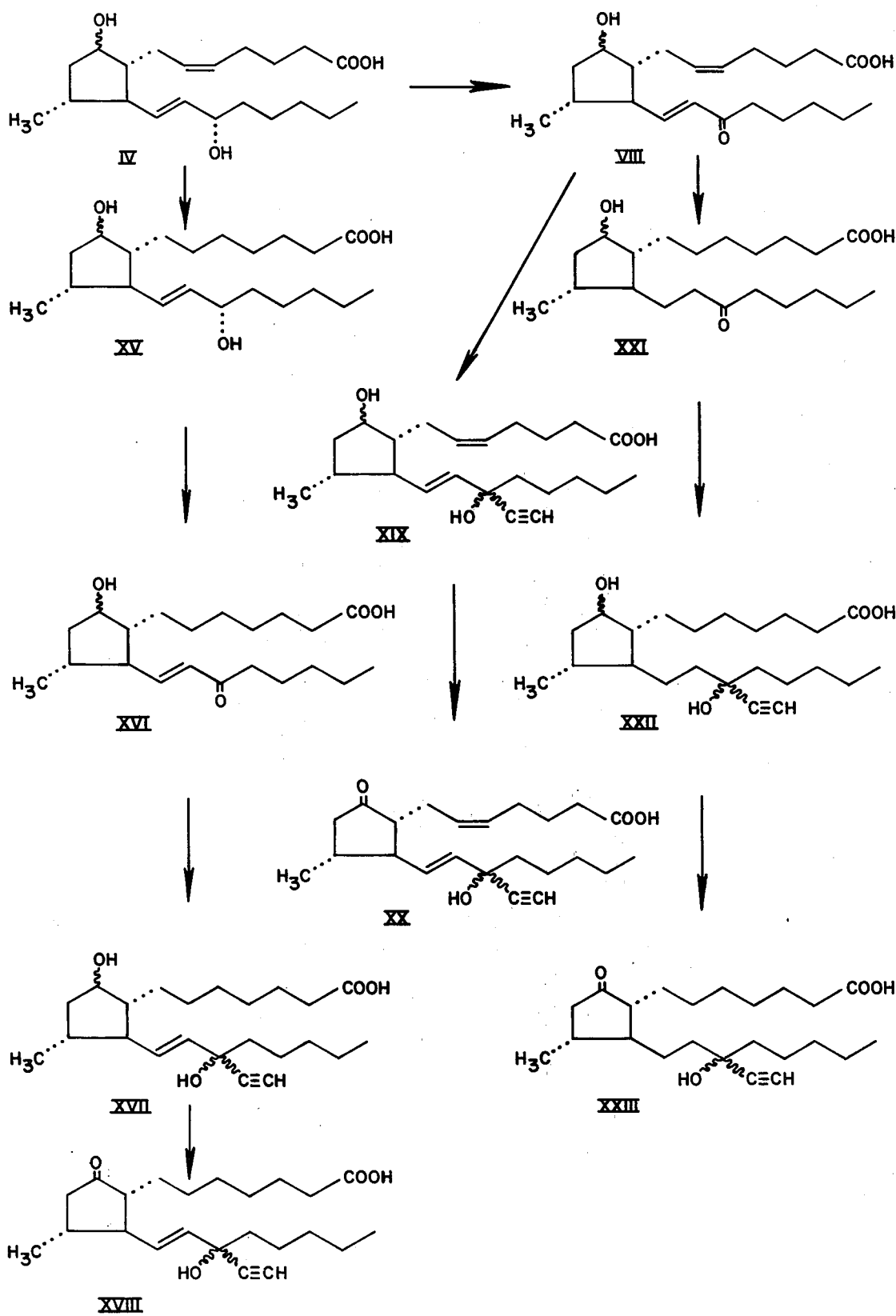

In describing the synthesis of the compositions of the invention, reference will be made to FIGS. 1, 2, and 3 wherein the formulae representing the various aspect of the invention are assigned Roman numerals for purposes of identification. Additionally, in order to designate the stereochemistry of various substituents on the prostaglandin skeleton, different types of lines are utilized when representing the bonds of said substituents. Thus, with reference to the plane of the paper, when a dashed line (- - -) is used, the substituent will be understood to be in the α (down) configuration; when a heavy line (▶-) is used, the substituent will be understood to be in the β (up) configuration; and when a wavy line (⌇) is used both α and β configurations are contemplated for the substituent. Thus, for example, when a new assymetric center is created by a below-described reaction, for example reduction of a ketone, since both possible configurations for the secondary alcohol will be produced the substituents will be denoted by a wavy line (⌇). Both of said isomers are considered to be full equivalents for the purposes of this invention. For purposes of convenience, the formulae in FIGS. 1, 2, and 3 are all free carboxylic acids; however, it will be obvious to those skilled in the art that these free acids may readily be esterified as for example with diazomethane, or with an alkanol and the proper catalyst. These esters are considered to be full equivalents to the free acids for the purposes of the invention. Finally, the use of specific embodiments in FIGS. 1, 2, and 3 to illustrate the invention is merely descriptive and is not intended to delimit the scope of the invention.

The starting materials for the synthesis of the compounds of the invention are PGA$_2$, its 15-epimer, and their respective esters. Referring now to FIG. 1, PGA$_2$ (which may be obtained from natural sources or may be prepared synthetically as described, for example, in South African Patent No. 66/3600) is first methylated in the 11-position by reaction with a methyl magnesium halide in the presence of cuprous chloride or cuprous iodide, or with methyl lithium copper (Me$_2$LiCu); for example when PGA$_2$ is reacted with methyl magnesium bromide, in the presence of cuprous chloride the 11- methyl compounds (I) and (II) are produced. These epimers may be separated as for example by fractional crystallization and chromatography. All further reactions described in this invention and represented in the figures will utilize the 11α-methyl isomer (I); however, utilization of the 11β-methyl isomer (II) in these below-described reactions is considered to the fully equivalent, and the corresponding 11β-methyl products derived therefrom are contemplated by the instant invention. The compound (I) is next treated with elemental hydrogen in the presence of a catalyst for example palladium on carbon, to reduce both carbon to carbon double bonds and produce (III). Alternatively, the carbonyl group of (I) may be reduced for example with sodium borohydride in methanol producing the epimeric alcohols (IV). Further, (I) may be oxidized with for example Jones reagent proucing the diketone (XXIV). Finally, (I) may be reacted with dihydropyran in the presence of a catalyst, for example p-toluenesulfonic acid producing (V) which by selective reduction of its 5-double bond affords (VI). This selective reduction is carried out in the presence of a catalyst such as 5% palladium on carbon, and is accomplished by stopping the reaction when one equivalent of hydrogen has been absorbed. The tetrahydropyranyl group of (VI) may be removed with dilute acid, for example dilute HCl producing the allylic alcohol (vII).

FIG. 2 describes the synthesis of embodiments of the invention wherein the 15-position (prostaglandin numbering system) is substituted with a methyl group. The starting material in FIG. 2 is compound (IV) which is prepared as described in FIG. 1. The allylic alcohol function of (VI) is first oxidized to produce the ketone (VIII). This oxidation may be accomplished by the use of 2,3-dichloro-5,6-dicyano-1,4-benzoquinone (DDQ) in an inert solvent such as dioxane.

Ideally, (VI) and DDQ are dissolved in dioxane, heated to about 55° for about 22 hours, the reaction mixture is filtered and the product isolated from the concentrated filtrate by chromatography. The ketone (VIII) is next reacted with a methyl metallic reagent, such as methyl magnesium bromide, producing the epimeric mixture (IX). Methyl lithium could also be utilized to produce (IX) from (VIII). The secondary alcohol function of (IX) can be oxidized, for example with Jones reagent, producing the ketone (X). Alternatively, the 5-double bond of (IX) may be selectively hydrogenated using tris(triphenylphosphine) rhodium (I) chloride as catalyst (see for example J. Labelled Compounds, 6, 395 [1970]) producing the mono ene (XI). The secondary alcohol function of (XI) may be oxidized with, for example, Jones reagent, producing the ketone (XII). Finally, both double bonds of (IX) may be reduced with elemental hydrogen in the presence of a catalyst such as 5% palladium on carbon producing (XIII). The secondary alcohol function of (XIII) may next be oxidized with for example Jones reagent producing the ketone (XIV).

FIG. 3 describes the synthesis of embodiments of the invention wherein the 15-position (prostaglandin numbering system) is substituted with an ethynyl group. The starting material in FIG. 3 is compound (IV) which is prepared as described in FIG. 1. The 5-double bond of compound (IV) may first be selectively reduced with elemental hydrogen using, for example, tris(triphenylphosphine) rhodium (I) chloride as catalyst to produce (XV). The allylic alcohol function of (XV) is next oxidized with, for example, DDQ, producing the ketone (XVI). This ketone is reacted with an ethynyl metallic reagent such as ethynyl magnesium bromide, producing the diol (XVII). Lithium acetylide could also be utilized to produce (XVII) from (XVI). The secondary alcohol function of (XVII) is next oxidized with, for example, Jones reagent, producing the ketone (XVIII). Alternatively the allylic alcohol function of (IV) may be oxidized with, for example, DDQ, producing the ketone (VIII) (Previously described in FIG. 2). The ketone function of (VIII) may be reacted with an ethynyl metallic reagent such as ethynyl magnesium bromide, producing the diol (XIX). Lithium acetylide could also be utilized to produce (XIX) from (VIII). The secondary alcohol function of (XIX) may next be oxidized with for example Jones reagent producing the ketone (XX). Finally, both carbon to carbon double bonds of (VIII) may be reduced with for example elemental hydrogen in the presence of 10% palladium on carbon as catalyst producing (XXI). The ketone function of (XXI) may be reacted with an ethynyl metallic reagent such as -ethynyl magnesium bromide, producing the diol (XXII). Lithium acetylide could also be utilized to produce (XXII) from (XXI). The secondary alcohol function of (XXII) may next be oxidized with for example Jones reagent producing the ketone (XXIII).

Various compounds of the invention bear carboxyl groups and can be readily converted to their respective alkali metal salts or a salt of a pharmacologically acceptable cation derived from ammonia or a basic amine. All such salts are full equivalents of the subject matter particularly claimed.

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 0.15 micrograms to about 50 micrograms, and preferably from about 0.15 to about 25 micrograms. The bronchodilation produced upon aerosol inhalation can be observed by the method of Rosenthale et al., J. Pharmacol. Exp. Ther., 178, 541 (1971).

In the use of the compounds of the invention to produce hypotensive effects in warm-blooded animals, administration by the injectable route is preferred, preferably the intravenous route.

Thus in the anesthetized dog by the intravenous route the dose to produce hypotension is from about 1 mg/kg. to about 200 mg/kg. and preferably from about 10 mg/kg. to about 100 mg/kg.

In the rat by the subcutaneous route the dose to inhibit gastric secretion is from about 0.1 mg/kg. to about 25 mg/kg. and preferably from about 0.5 mg/kg. to about 10 mg/kg. The reduction in gastric secretion can be observed by a modification of the method of Shay et al., Gastroenterology, 26, 906 (1954).

The following examples further illustrate the best mode contemplated by the inventors for the practice of the invention.

EXAMPLE 1

7-[2β-[(3S)*-3-Hydroxy-Trans-1-Octenyl]-3α-Methyl-5-Oxo-1α-Cyclopentyl]-Cis-5-Heptenoic Acid (I) and 7-2β-[(3S)-3-Hydroxy-Trans-1-Octenyl]-3β-Methyl-5-Oxo-1α-Cyclopentyl]-Cis-5-Heptenoic Acid (II)

A solution of 3.0 g. of PGA$_2$ in 60 ml. of THF was added dropwise to an ice-cooled mixture of 24 ml. of 3M methyl magnesium bromide and 5.0 g. of cuprous chloride in 120 ml. of THF and stirred a 0° C. for 1 hour. The mixture was added to aqueous ammonium chloride solution and extracted with ether. After washing with water and drying over magnesium sulfate, the extract was concentrated to give crystalline material. Filtration followed by recrystallization from ether-pentane afforded 1.2 g. of 7-[2β-[(3S)*-3-hydroxy-trans-1-octenyl]-3α-methyl-5-oxo-1α-cyclopentyl]-cis-5-heptenoic acid, m.p. 68°–70° C., $\lambda_{max}^{KBr}$ 3.0 (shoulder), 3.5, 5.8, 6.9, 7.6, 8.05, 8.55, 10.3 μ. NMR: δ 6.93 (s, 2, OH), 5.54 (m, 13 and 14-H), 5.38 (m, 5 and 6-H), 4.16 (m, 1, 15-H). Mass spectrum: M$^+$ at m/e 350.2476 (theory 350.2455).

Evaporation of the filtrates and silica chromatography of the residue with 30% ethylacetate in hexane followed by crystallization from ether-pentane gave 0.09 g. of 7-[2β-[(3S)-3-hydroxy-trans-1-octenyl]-3-β-methyl-5-oxo-1α-cyclopentyl]-cis-5-heptenoic acid, m.p. 72°–74° C., $\lambda_{max}^{film}$ 3.0 (shoulder), 3.5, 5.8 (shoulder), 5.9, 7.0, 8.15, 8.45, 10.4 μ. NMR: δ 7.05–6.22 (m, 2, OH), 5.45 (m, 4, olefinic), 4.15 (m, 1, 15-H) ppm. Mass spectrum: M$^+$ at m/e 350.2460 (theory 350.2455).

*S=natural stereochemistry, R=epimeric stereochemistry ("Prostaglandins", U.S. von Euler & R. Eliasson, p. 16, Academic Press, New York 1967).

EXAMPLE 2

2β-[(3S)-Hydroxyoctyl]-3α-Methyl-5-Oxo-1α-Cyclopentane Heptanoic Acid (III)

A solution of 0.9 g. of 7-(2β-[(3S)-3-hydroxy-trans-octenyl]-3α-methyl-5-oxo-1α-cyclopentyl)-cis-5-heptenoic acid in 10 ml. of methanol was added to a prehydrogenated mixture of 0.2 g. of 5% Pd/C in 155 ml. of methanol and the mixture hydrogenated at 25° and atmospheric until two equivalents of hydrogen were absorbed. After filtering, the solution was evaporated and the residue chromatographed on silica. Elution with 25% ethylacetate in hexane followed by recrystallization from ethylacetate-hexane afforded 0.25 g. of 2β-[(3S)-3-hydroxyoctyl]-3α-methyl-5-oxo-1α-cyclopentane heptanoic acid, m.p. 43.5°–44.5° C., $\lambda_{max}^{KBr}$ 3.0, 3.5, 5.8, 6.85, 8.5, 8.9 μ. NMR: δ 6.81 (s, 2, OH), 3.65 (m, 1, 15-H) ppm. Mass spectrum: M$^+$ at m/e 354.2771 (theory 354.2768).

EXAMPLE 3

7-(3α-Methyl-5-Oxo-2β-[(3S)-3-(Tetrahydropyran-2-Yloxy)-Trans-1-Octenyl]-1α-Cyclopentyl)-Cis-5-Heptenoic (V)

A solution of 1.0 g. of 7-(2β-[(3S)-3-hydroxy-trans-1-octenyl]-3α-methyl-5-oxo-1α-cyclopentyl)-cis-5-heptenoic acid and 0.3 g. of dihydropyran in 25 ml. of benzene was treated with 0.02 g. of p-toluenesulfonic acid and stirred for 1.5 hours. The mixture was diluted with water and extracted with ether. After washing with water and drying over magnesium sulfate, the extract was evaporated and the residue chromatographed on silica. Elution with 20% ethyl acetate in hexane afforded 1.0 g. of 7-(3α-Methyl-5-oxo-2β-[(3S)-3-(tetrahydropyran-2-yloxy)-trans-1-octenyl]-1α-cyclopentyl)-cis-5-heptenoic as an oil, $\lambda_{max}^{film}$ 3.1(shoulder), 3.35, 5.65, 5.78, 9.74, 10.2 μ. Mass spectrum: M$^+$ at m/e 434 (theory 434), M$^+$-PyOH at m/e 332.2328 (theory 332.2350).

EXAMPLE 4

3α-Methyl-5-Oxo-2β-[3S)-3-(Tetrahydropyran-2-Yloxy)-Trans-1-Octenyl] -1α-Cyclopentaneheptanoic Acid (VI)

A solution of 1.0 g. of 7-[3α-methyl-5-oxo-2β-[(3S)-3-(tetrahydropyran-2-yloxy)-trans-1-octenyl]-1α-cyclopentyl]-cis-5-heptenoic acid in 10 ml. of methanol was added to the prehydrogenated mixture of 0.2 g. of 5% Pd/C in 155 ml. of methanol and the mixture hydrogenated at 25°C under atmospheric pressure until one equivalent of hydrogen was absorbed. After filtering the solution was evaporated to afford 0.9 ml. of 3α-Methyl-5-oxo-2β-[3S)-3-(tetrahydropyran-2-yloxy)-trans-1-octenyl]-1α-cyclopentaneheptanoic acid as an oil. NMR: δ 9.55 (s, 1, OH), 8.55 (m, 2, 13 and 14-H) ppm. IR: $\lambda_{max}^{film}$ 3.4, 5.7, 5.8, 9.8, 10.3 μ.

EXAMPLE 5

3α-Methyl-2β-[(3S)-3-Hydroxy-Trans-1-5-Oxo-1α-Cyclopentaneheptanoic Acid (VII)

A solution of 0.9 g. of 3α-methyl-5-oxo-2β-[(3S)-3-(tetrahydropyran-2-yloxy)-trans-1-octenyl]-1α-cyclopentaneheptanoic acid in 60 ml. of THF was treated at 25°C with 60 ml. of 1N HCl and stirred for 3.5 hours. The mixture was diluted with water and extracted with ether. After washing with water and drying over magnesium sulfate, the extract was evaporated and the residue chromatographed on silica. Elution with 25% ethylacetate in hexane followed by recrystallization from ethyl acetate afforded 0.31 g. of 3α-Methyl-2β-[(3S)-3-hydroxy-trans-1-octenyl]-5-oxo-1α-cyclopentaneheptanoic acid, m.p. 115°–116°C, $\lambda_{max}^{KBr}$ 3.0, 3.45, 5.75, 6.8, 7.55, 7.8, 8.1, 8.45, 8.9, 9.45, 9.8, 10.2 μ. NMR: δ 6.43 (s, 2, OH), 5.88 (d, J=3, 13 and 14-H), 4.16 (m, 1, 15-H) ppm. Mass spectrum: M$^+$ at m/e 352 (theory 352).

EXAMPLE 6

7-(5α-Hydroxy-2β-[(3S)-3-Hydroxy-Trans-1-Octenyl]-3α-Methyl-1α-Cyclopentyl)-Cis-5-Heptanoic Acid (9α-IV) and 7-(5β-Hydroxy-2β-[(3S))-3-Hydroxy-1-Octenyl]-3α-Methyl-1α-Cyclopentyl)-Cis-5-Heptanoic Acid (9β-IV)

An ice-cooled solution of 7.8 g. of 7-(2β-[(3S)-3-hydroxy-trans-1-octenyl]-3α-methyl-5-oxo-1α-cyclopentyl)-cis-5-heptenoic acid in 150 ml. of methanol was treated with 3.5 g. of sodium borohydride and stirred at 0°C for 2 hours. The mixture was diluted with water and acidified with acetic acid. Extraction of the resulting mixture with ether, followed by washing, drying and evaporation of the extract gave the crude product. Silica chromatography with 30% ethyl acetate in hexane afforded 3.5 g. of 7-(5α-Hydroxy-2β-[(3S)-3-hydroxy-trans-1-octenyl]-3α-methyl-1α-cyclopentyl)-cis-5-heptenoic acid as an oil, $\lambda_{max}^{film}$ 3.0, 3.5, 5.85, 6.9, 7.15, 8.1, 8.9, 9.8, 10.35 μ. NMR: μ 5.57 (s, 3, OH), 6.0–5.17 (m, 4, olefinic), 4.21 (m, 2, 9 and 15-H), 1.01 (d J=4.5, 11-methyl) ppm. Mass spectrum: M+ at m/e 352.2670 (theory 352.2613).

Further elution with 30% ethyl acetate in hexane afforded 3.0 g. of 7-(5β-hydroxy-1-octenyl]-3α-methyl-1α-cyclopentyl)-cis-5-heptenoic acid as an oil, $\lambda_{max}^{film}$ 3.0, 3.5, 5.85, 6.9, 7.15, 8.2, 10.4 μ. NMR: δ 5.61 (s, 3, OH), 5.52 (s, 4, olefinic), 4.10 (m, 2, 9 and 15-H), 0.91 (d, J=4.5, 11-methyl) ppm. Mass spectrum: M+ at m/e 352 (theory 352), M+−H$_2$O at m/e 334.2564 (theory 334.2507).

EXAMPLE 7

7-[5α-Hydroxy-3α-Methyl-2β-(3-Oxo-Trans-1-Octenyl)-1α-Cyclopentyl]-Cis-5-Heptenoic Acid (9α-VIII)

A solution of 3.3 g. of 7-(5α-hydroxy-2β-[(3S)-3-hydroxy-trans-1-octenyl]-3α-methyl-1α-cyclopentyl)-cis-5-heptenoic acid and 3.0 g. of 2,3-dichloro-5,6-dicyano-1,4-benzoquinone in 100 ml. of dioxane was stirred at 55° C. for 22 hours. After filtering, the solution was evaporated and the residue chromatographed on silica. Elution with 25% ethyl acetate in hexane afforded 2.9 g. of 7-[5α-hydroxy-3α-methyl-2β-(3-oxo-trans-1-octenyl)-1α-cyclopentyl]-cis-5-heptenoic acid as an oil, $\lambda_{max}^{film}$ 3.0 (shoulder), 3.5, 5.85, 6.0, 6.2, 6.9, 8.2 (broad), 10.25 μ. UV $\lambda_{max}^{EtOH}$ 223 mμ (ε 14,000). NMR: δ 6.75 (dd, J=16, 7.5, 13-H), 6.32 (s, 2, OH), 6.19 (d, J=16, 14-H), 5.48 (m, 2, 5 and 6-H), 4.32 (m, 1, 9-H) ppm. Mass spectrum: M+ at m/e 350.2499 (theory 350.2455).

EXAMPLE 8

7-[5β-Hydroxy-3α-Methyl-2β-(3-Oxo-Trans-1-Octenyl)-1α-Cyclopentyl]-Cis-5-Heptenoic Acid (9β-VIII)

A solution of 2.5 g. of 7-(5β-hydroxy-2β-[(3S)-3-hydroxy-trans-1-octenyl]-3α-methyl-1α-cyclopentyl)-cis-5-heptenoic acid and 2.5 g. of 2,3-dichloro-5,6-dicyano-1,4-benzoquinone in 80 ml. of dioxane was stirred at 55° C. for 22 hours. After filtering, the solution was evaporated and the residue chromatographed on silica. Elution with 25% ethyl acetate in hexane afforded 2.1 g. of 7-[5β-hydroxy-3α-methyl-2α-(3-oxo-trans-1-octenyl)-1α-cyclopentyl]-cis-5-heptenoic acid as an oil, $\lambda_{max}^{film}$ 3.0 (shoulder), 3.5, 5.9, 6.05, 6.2, 6.9, 7.15, 7.2, 8.15, 10.25 μ. UV: $\lambda_{max}^{EtOH}$ 232 mμ (ε 13,300). NMR: δ 6.77 (dd, J=7.5, 15.7, 13-H), 6.72 (s, 2, OH), 6.14 (d, J=15.7, 14-H), 5.5 (t, 2, 5 and 6-H),4.02(n,1,9-H) ppm. Mass spectrum: M+ at m/e 350.2492 (theory 350.2455).

EXAMPLE 9

7-(5α-Hydroxy-2β-[(3RS)*-3-Hydroxy-3-Methyl-Trans-1-Octenyl]-3α-Methyl-1α-Cyclopentyl)-Cis-5-Heptenoic Acid (9α-IX)

An ice-cooled solution of 1.0 g. of 7-[5α-hydroxy-3α-methyl-2β-(3-oxo-trans-1-octenyl)-1α-cyclopentyl]-cis-5-heptenoic acid in 50 ml. of THF was treated with 8 ml. of 3M methyl magnesium bromide and stirred at 0° C. for two hours. The mixture was added to aqueous ammonium chloride solution and extracted with ether. After washing with water and drying over magnesium sulfate, the extract was evaporated and the residue chromatographed on silica. Elution with 25% ethyl acetate in hexane afforded 7-(5α-hydroxy-2β-(3RS)*-3-hydroxy-3-methyl-trans-1-octenyl]-3α-methyl-1α-cyclopentyl)-cis-5-heptenoic acid as an oil, $\lambda_{max}^{film}$ 3.0, 3.5, 5.85, 6.9, 8.95, 9.75, 10.33 μ. NMR: δ5.8–5.2 (m, 4, olefinic), 5.43 (s, 3, OH), 4.30 (m, 1, 11-H), 1.30 (s, 15-methyl), 1.0 (d, J=5, 11-methyl) ppm. Mass spectrum: M+−H$_2$O at m/e 348.2682 (theory 348.2664).

*RS=isomeric mixture

EXAMPLE 10

7-(5β-Hydroxy-2β-[(3RS)-3-Hydroxy-3-Methyl-Trans-1-Octenyl]-3α-Methyl-1α-Cyclopentyl)-Cis-5-Heptenoic Acid (9β-IX)

An ice-cooled solution of 0.9 g. of 7-[5β-hydroxy-3α-methyl-2β-(3-oxo-trans-1-octenyl)-1α-cyclopentyl]-cis-5-heptenoic acid in 25 ml. of THF was treated with 8 ml. of 3M methyl magnesium bromide and stirred at 0° C. for 2 hours. The mixture was added to aqueous ammonium chloride solution and extracted with ether. After washing with water and drying over magnesium sulfate, the extract was evaporated and the residue chromatographed on silica. Elution with 25% ethyl acetate in hexane afforded 0.65 g. of 7-(5β-hydroxy-2β-[3RS)-3-hydroxy-3-methyl-trans-1-octenyl]-3α-methyl-1α-cyclopentyl)-cis-5-heptenoic acid as an oil, $\lambda_{max}^{film}$ 3.0, 3.45, 5.85, 6.9, 7.3, 8.15, 10.3 μ. NMR: δ 5.45 (m, 4, olefinic), 5.32 (s, 3, OH), 3.80 (m, 1, 9-H), 1.28 (s, 15-methyl) ppm. Mass spectrum: M+ at m/e 366.2811 (theory 366.2769).

EXAMPLE 11

7-(2β-[(3RS)-3-Hydroxy-3-Methyl-Trans-1-Octenyl]-5-Oxo-3α-Methyl-1α-Cyclopentyl)-Cis-5-Heptenoic Acid (X)

An ice-cooled solution of 0.15 g. of 7-(5β-hydroxy-2β-(3RS)-3-hydroxy-3-methyl-trans-1-octenyl]-3α-methyl-1α-cyclopentyl)-cis-5-heptenoic acid in 10 ml. of acetone was treated with 0.6 ml. of 1.2 M Jones reagent and stirred at 0° C. for three-fourth's hour. The mixture was treated with 2 ml. of methanol and neutralized with aqueous sodium bicarbonate solution. After acidification with acetic acid, the mixture was extracted with ether and the extract was washed with water and dried with magnesium sulfate. Evaporation of the solvent and silica chromatography of the residue with 20% ethyl acetate in hexane afforded 0.07 g. of 7-(2β-[(3RS)-3-hydroxy-3-methyl-trans-1-octenyl]-5-oxo-3α-methyl-1α-cyclopentyl)-cis-5-heptenoic acid as an oil, $\lambda_{max}^{film}$ 2.95 (shoulder), 3.4, 5.75, 6.8, 7.1, 8.05, 8.55, 10.25 μ. NMR: δ 6.5 (s, 2, OH), 5.5 (m, 4, olefinic), 1.32 (s, 15-methyl), 1.10 (m, 11-methyl) ppm. Mass spectrum: M+ −H$_2$O at m/e 346.2535 (theory 346.2507).

EXAMPLE 12

5α-Hydroxy-2β-[(3RS)-3-Hydroxy-3-Methyl-Trans-1-Octenyl]-3α-Methyl-1α-Cyclopentane Heptanoic Acid (9α-XI)

A solution of 0.48 g. of 7-(5α-hydroxy-2β-[(3RS)-3-hydroxy-3-methyl-trans-1-octenyl)-3α-methyl-1α-cyclopentyl)-cis-5-heptenoic acid and 0.2 g. of tris (triphenylphosphine) rhodium (I) chloride in 22 ml. of a mixture of ethanol-benzene (1:1) was hydrogenated at 25° C. and atmospheric pressure until one equivalent of hydrogen was absorbed. The solution was evaporated and the residue chromatographed on silica. Elution with 22% ethylacetate in hexane afforded 0.3 g. of 5α-hydroxy-2β-[(3RS)-3-hydroxy-3-methyl-trans-1-octenyl]-3α-methyl-1α-cyclopentane heptanoic acid as an oil (solidified on standing, $\lambda_{KBr}^{film}$ 2.95, 3.4, 3.5 (shoulder), 5.82, 6.9, 7.25, 8.1, 8.8, 9.3, 10.2, 10.43 μ. NMR: δ 5.42 (m, 2, 13 and 14-H), 5.08 (s, 3, OH), 4.22 (m, 1, 9-H), 0.98 (d, J=4.5, 11-methyl) ppm. Mass spectrum: M+ —H₂O at m/e 350.2840 (theory 350.2820).

EXAMPLE 13

5β-Hydroxy-2β-[(3RS)-3-Hydroxy-3-Methyl-Trans-1-Octenyl]-3β-Methyl-1α-Cyclopentaneheptanoic Acid (9β-XI)

A solution of 0.5 g. of 7-(5β-hydroxy-2β-[(3RS)-3-hydroxy-3-methyl-trans-1- octenyl]-3α-methyl-1α-cyclopentyl)-cis-5-heptenoic acid and 0.2 g. of tris(triphenylphosphine) rhodium (I) chloride in 35 ml. of a mixture of ethanol-benzene (1:1) was hydrogenated at 25° C. and atmospheric pressure until one equivalent of hydrogen was absorbed. The solution was evaporated and the residue chromatographed on silica. Elution with 20% ethyl acetate in hexane afforded 0.44 g. of 5β-hydroxy-2β-[(3RS)-3-hydroxy-3-methyl-trans-1-octenyl]-3α-methyl-1α-cyclopentaneheptanoic acid as an oil, $\lambda_{max}^{film}$ 3.0, 3.45, 5.82, 6.85, 8.23, 10.3 μ. NMR: δ 5.47 (m, 2, 13 and 14-H), 5.07 (s, 3, OH), 3.95 (m, 1, 9-H), 0.91 (d, J=4.5, 11-methyl) ppm. Mass spectrum: M+—H₂O at m/e 350.2824 (theory 350.2820).

EXAMPLE 14

2β-[(3RS)-3-Hydroxy-3-Methyl-Trans-1-Octenyl]-3α-Methyl-5-Oxo-1α-Cyclopentane Heptanoic Acid (XII)

An ice-cooled solution of 0.35 g. of 5β-hydroxy-2β-[(3RS)-3-hydroxy-3-methyl-trans-1-octenyl]-3α-methyl-1α-cyclopentane heptanoic acid in 20 ml. of acetone was treated with 1.8 ml. of 1.2 M Jones reagent and stirred at 0° C. for three-fourths hours. The mixture was treated with 2 ml. of methanol and neutralized with aqueous sodium bicarbonate solution. After acidification with acetic acid, the mixture was extracted with ether and the extract was washed with water and dried with magnesium sulfate. Evaporation of the solvent and silica chromatography of the residue with 20% ethyl acetate in hexane afforded 0.28 g. of 2β-[(3RS)-3-hydroxy-3-methyl-trans-1-octenyl]-3α-methyl-5-oxo-1α-cyclopentane heptanoic acid as an oil, $\lambda_{max}^{film}$ 3.0, 3.45, 5.75, 6.8, 7.1, 7.22, 8.55, 10.22 μ. NMR: δ 6.39 (s, 2, OH), 5.55 (m, 2, 13 and 14-H), 2.31 (t, —CH₂CO₂—) 1.29 (s, 15-methyl), 1.04 (m, 11-methyl) ppm. Mass spectrum: M+ at m/e 366 (theory 366), M+—H₂O at m/e 348.2680 (theory 348.2664).

EXAMPLE 15

5α-Hydroxy-2β-[(3RS)-3-Hydroxy-3-Methyloctyl]-3α-Methyl-1α-Cyclopentane Heptanoic Acid (XIII)

A solution of 0.42 g. of 7-(5α-hydroxy-2β-[(3RS)-3-hydroxy-3-methyl-trans-1-octenyl]-3α-methylcyclopentyl)-cis-5-heptenoic acid in 10 ml. of ethyl acetate was added to the prehydrogenated mixture 0.1 g. of 5% Pd/C in 5 ml. of ethyl acetate and the mixture hydrogenated at 25° C. under atmospheric pressure until two equivalents of hydrogen were absorbed. After filtering, the solution was evaporated and the residue chromatographed on silica. Elution with 20% ethyl acetate in hexane afforded 0.38 g. of 5α-hydroxy-2β-[(3RS)-3-hydroxy-3-methyloctyl]-3α-methyl-1α-cyclopentane heptanoic acid as an oil, $\lambda_{max}^{film}$ 3.0, 3.45, 5.85, 6.85, 7.38, 8.25, 8.85 μ. NMR: δ 4.66 (s, 3, OH), 4.19 (m, 1, 9-H), 2.33 (t, —CH₂CO₂—), 1.17 (s, 15-methyl), 1.07 (d, J=5.5, 11-methyl) ppm. Mass spectrum: M+—H₂O at m/e 352.2971 (theory 352.2977).

EXAMPLE 16

2β-[(3RS)-3-Hydroxy-3-Methyloctyl]-3α-Methyl-5-Oxo-1α-Cyclopentane Heptanoic Acid (XIV)

An ice-cooled solution of 0.3 g. of 5α-hydroxy-2β-[(3RS)-3-hydroxy-3-methyloctyl]-3α-methyl-1α-cyclopentane heptanoic acid in 15 ml. of acetone was treated with 0.8 ml. of 1.2 M Jones reagent and stirred at 0° C. for three-fourths hour. The mixture was treated with 1 ml. of methanol and neutralized with aqueous sodium bicarbonate solution. After acidification with acetic acid, the mixture was extracted with ether and the extract was washed with water and dried with magnesium sulfate. Evaporation of the solvent and silica chromatography of the residue with 25% ethyl acetate in hexane afforded 0.21 g. of 2β-[(3RS)-3-hydroxy-3-methyloctyl]-3α-methyl-5-oxo-1α-cyclo-pentane heptanoic acid as an oil, $\lambda_{max}^{film}$ 3.0, 3.45, 5.8, 6.87, 7.15, 7.3, 8.68 μ. NMR: δ 6.08 (s, 2, OH), 2.30 (t, —CH₂CO₂—), 1.18 (s, 15-methyl), 1.11 (d, J=5, 11-methyl) ppm. Mass spectrum: M+at m/e 368 (theory 368), M+—H₂O at m/e 350.2834 (theory 350.2820).

EXAMPLE 17

5α-Hydroxy-2β-[(3S)-3-Hydroxy-Trans-1-Octenyl]-3α-Methyl-1α-Cyclopentane Heptanoic Acid (9α-XV)

A solution of 0.2 g. of 7-(5α-hydroxy-2β-[(3S)-3-hydroxy-trans-1-octenyl]-3α-methyl-1α-cyclopentyl)-cis-5-heptenoic acid and 0.1 g. of tris(triphenylphosphine) rhodium (I) chloride in 25 ml. of a mixture of ethanol-benzene (1:1) was hydrogenated at 25° C. and atmospheric pressure until one equivalent of hydrogen was absorbed. The solution was evaporated and the residue chromatographed on silica. Elution with 20% ethyl acetate in hexane followed by recrystallization from chloroform-hexane afforded 0.05 g. of 5α-hydroxy-2β-[(3S)-3-hydroxy-trans-1-octenyl]-3α-methyl-1α-cyclopentane heptanoic acid, m.p. 94°–95° C., $\lambda_{max}^{KBr}$ 3.0, 3.45, 5.83, 6.83, 8.9, 9.9, 10.35 μ. NMR: δ 5.42 (m, 2, olefinic), 5.21 (s, 3, OH), 4.20 (m, 2, 9 and 15-H), 1.03 (d, J=4.5, 11-methyl) ppm. Mass spectrum: M+ —H₂O at m/e 336.2644 (theory 336.2663).

EXAMPLE 18

5β-Hydroxy-2β-[(3S)-3-Hydroxy-Trans-1-Octenyl]-3α-Methyl-1α-Cyclopentane Heptanoic Acid (9β-XV)

A solution of 0.19 g. of 7-(5β-hydroxy-2β-[(3S)-3-hydroxy-1-octenyl]-3α-methyl-1α-cyclopentyl)-cis-5-heptenoic acid and 0.2 g. of tris(triphenylphosphine) rhodium (I) chloride in 35 ml. of a mixtureof ethanol-benzene (1:1) was hydrogenated at 25° C. and atmospheric pressure until one equivalent of hydrogen was absorbed. The solution was evaporated and the residue chromatographed on silica. Elution with 20% ethyl acetate in hexane afforded 0.11 g. of 5β-hydroxy-2β-[(3S)-3S)-3-hydroxy-trans-1-octenyl]-3α-methyl-1α-cyclopentane heptanoic acid as an oil, $\lambda_{max}^{film}$ 3.0, 3.45, 5.82, 6.85, 8.23, 10.3 μ. NMR: δ 5.47 (m, 2, 13 and 14-H), 5.07 (s, 3, OH), 3.95 (m, 1, 9-H), 0.91 (d, J=4; 11-methyl) ppm. Mass spectrum: M$^+$ at m/e 354.2785 (theory 354.2768).

EXAMPLE 19

5α-Hydroxy-3α-Methyl-2β-[(3-Oxo-Trans-1-Octenyl)-1α-Cyclopentane Heptanoic Acid (XVI)

A solution of 2.1 g. of 5α-hydroxy-2β-[(3S)-3-hydroxy-trans-1-octenyl]-3α-methyl-1α-cyclopentane heptanoic acid and 1.5 g. of 2,3-dichloro-5,6-dicyano-1,4-benzoquinone in 65 ml. of dioxane was stirred at 70° C. for 24 hours. After filtering, the solution was evaporated and the residue chromatographed on silica. Elution with 20% ethyl acetate in hexane afforded 1.9 g. of 5α-hydroxy-3α-methyl-2β-[3-oxo-trans-1-octenyl]-1α-cyclopentane heptanoic acid as an oil, $\lambda_{max}^{film}$ 2.95 (shoulder), 3.4, 5.85, 6.0, 6.15, 6.85, 7.1, 8.2, 8.9, 10.2 μ. UV: $\lambda_{max}^{EtOH}$ 233 mμ (ε 13,000). NMR: δ 6.55 (d, d, J=15.5, 7.5, 13-H), 6.16 (s, 2, OH), 6.07 (d, J=15.5, 14-H), 4.22 (m, 1, 9-H), 1.00 (d, J=5, 11-methyl) ppm. Mass spectrum: QM$^+$ at m/e 353 (theory 353).

EXAMPLE 20

2β-[(3RS)-3-Ethynyl-3-Hydroxy-Trans-1-Octenyl]-5α-Hydroxy- 3α-Methyl-1α-Cyclopentane Heptanoic Acid (XVII)

A solution of 1.7 g. of 5α-hydroxy-3α-methyl-2β-[3-oxo-trans-1-octenyl]-1α-cyclopentane heptanoic acid in 20 ml. of THF was added at 0° C. to ethynyl-magnesium bromide (prepared from 40 ml. of 3M MeMgBr and excess acetylene) in 154 ml. of THF and stirred for 1 hour. The mixture was treated with aqueous ammonium chloride solution and extracted with ether. After washing with water and drying with magnesium sulfate, the extract was evaporated and the residue chromatographed on silica. Elution with 20% ethyl acetate in hexane afforded 1.2 g. of 2β-[(3RS)-3-ethynyl-3-hydroxy-trans-1-octenyl]-5α-hydroxy-3α-methyl-1α-cyclopentane heptanoic acid as an oil, $\lambda_{max}^{film}$ 3.03, 3.48, 5.8, 6.8, 7.06, 7.22, 8.85, 10.25 μ. NMR: δ 5.55 (m, 2, 13 and 14-H), 4.22 (m, 1, 9-H), 2.56 (s, 1, C ≡ CH), 1.01 (d, J=4.5, 11-methyl) ppm. Mass spectrum: QM$^+$ at m/e 379 (theory 379).

EXAMPLE 21

2β-[(3RS)-3-Ethynyl-3-Hydroxy-Trans-1-Octenyl]-5-Oxo-3α-Methyl-1α-Cyclopentane Heptanoic Acid (XVIII)

An ice-cooled solution of 1.1 g. of 2β-[(3RS)-3-ethynyl-3-hydroxy-trans-1-octenyl]-5α-hydroxy-3α-methyl-1α-cyclopentane heptanoic acid in 125 ml. of acetone was treated with 5 ml. of 1.2M Jones reagent and stirred at 0° C. for three-fourths hour. The mixture was treated with 5 ml. of methanol and neutralized with aqueous sodium bicarbonate solution. After acidification with acetic acid, the mixture was extracted with ether and the extract was washed with water and dried with magnesium sulfate. Evaporation of the solvent and silica chromatography of the residue with 20% ethyl acetate in hexane afforded 0.55 g. of 2β-[(3RS)-3-ethynyl-3-hydroxy-trans-1-octenyl]-5-oxo-3α-methyl-1α-cyclopentane heptanoic acid as an oil, $\lambda_{max}^{film}$ 3.05, 3.4, 5.78, 6.8, 7.08, 7.2, 8.0, 8.55, 9.8, 10.27 μ. NMR: δ 6.6 (m, 2, OH), 5.72 (m, 2, 13 and 14-H), 2.62 (s, 1, C ≡ CH), 1.12 (m, 11-methyl) ppm. Mass spectrum: M$^+$ at m/e 376.2668 (theory 376.2612).

EXAMPLE 22

7-(2β-[(3RS)-3-Ethynyl-3-Hydroxy-Trans-1-Octenyl]-5α-Hydroxy-3α-Methyl-1α-Cyclopentyl)-Cis-5-Heptenoic Acid (9α-XIX)

A solution of 0.18 g. of 7-[5α-hydroxy-3α-methyl-2β-(3-oxo-trans-1-octenyl)-1α-cyclopentyl]-cis-5-heptenoic acid in 5 ml. of THF was added at 0° C. to ethynyl magnesium bromide (prepared from 8.0 ml. of 3M MeMgBr and excess acetylene) in 120 ml. of THF and stirred for 1½ hours. The mixture was treated with aqueous ammonium chloride solution and extracted with ether. After washing with water and drying with magnesium sulfate, the extract was evaporated and the residue chromatographed on silica. Elution with 20% ethyl acetate in hexane afforded 0.11 g. of 7-(2β-[(3RS)-3-ethynyl-3-hydroxy-trans-1-octenyl]-5α-hydroxy-3α-methyl-1α-cyclopentyl)-cis-5-heptenoic acid as an oil, $\lambda_{max}^{film}$ 3.05, 3.45, 5.83, 6.85, 8.1, 9.9, 10.32 μ. NMR: δ 5.67 (m, 4, olefinic), 5.60 (s, OH), 4.30 (m, 1, 9-H), 2.60 (s, 1, C ≡ CH), 1.03 (d, J=5, 11-methyl) ppm. Mass spectrum: M$^+$ at m/e 376.2587 (theory 378.2612).

EXAMPLE 23

7-(2β-[(3RS)-3-Ethynyl-3-Hydroxy-Trans-1-Octenyl]-5β-Hydroxy-3α-Methyl-1α-Cyclopentyl)-Cis-5-Heptenoic Acid (9β-XIX)

A solution of 0.64 g. of 7-[5β-hydroxy-3α-methyl-2β-(3-oxo-trans-1-octenyl)-1α-cyclopentyl]-cis-5-heptenoic acid in 40 ml. of THF was added to 0° C. to ethynyl magnesium bromide (prepared from 13 ml. of 3M MeMgBr and excess acetylene) in 150 ml. of THF and stirred for 1 hour. The mixture was treated with aqueous ammonium chloride solution and extracted with ether. After washing with water and drying with magnesium sulfate, the extract was evaporated and the residue chromatographed on silica. Elution with 25% ethyl acetate in hexane afforded 0.50 g. of 7-(2β-[(3RS)-3-ethynyl-3-hydroxy-trans-1-octenyl]-5β-hydroxy-3α-methyl-1α-cyclopentyl)-cis-5-heptenoic acid as an oil, $\lambda_{max}^{film}$ 3.04, 3.45, 5.77, 6.82, 8.05, 10.28 μ. NMR: δ 5.56 (m, 4, olefinic), 5.2 (s, 3, OH), 3.99 (m, 1, 9-H), 2.56 (s, 1, C ≡ CH), 0.93 (d, J=4.5, 11-methyl) ppm. Mass spectrum: M$^+$ at m/e 368 (theory 368), M$^+$ at m/e 368 (theory 368), M$^+$ —H$_2$O at m/e 350.2834 (theory 350.2820).

EXAMPLE 24

7-[2β-(3ξ*-Ethynyl-3ξ*-Hydroxy-Trans-1-Octenyl)-3α-Methyl-5-Oxo-1α-Cyclopentyl]-Cis-5-Heptenoic Acid (XX) and 7-[2β-(3ξ-Ethynyl-3ξ-Hydroxy-Trans-1-Octenyl)-3α-Methyl-5-Oxo-1α-Cyclopentyl]-Cis-5-Heptenoic Acid An ice-cooled solution of 0.4 g. of 7-(2β-[(3RS)-3-ethynyl-3-hydroxy-trans-1-octenyl]-5β-hydroxy-3α-methyl-1α-cyclopentyl)-cis-5-heptenoic acid in 20 ml. of acetone was treated with 2 ml. of 1.2M Jones reagent and stirred at 0° C. for three-fourths hours. The mixture was treated with 2 ml. of methanol and neutralized with aqueous sodium bicarbonate solution. After acidification with acetic acid, the mixture was extracted with ether and the extract was washed with water and dried with magnesium sulfate. Evaporation of the solvent and silica chromatography of the residue with 17% ethyl acetate in hexane afforded 0.1 g. of 7-[2β-(3ξ*-ethynyl-3ξ*-hydroxy-trans-1-octenyl)-3α-methyl-5-oxo-1α-cyclopentyl]-cis-5-heptenoic acid as an oil, $\lambda_{max}^{film}$ 3.07, 3.4, 5.87, 6.85, 7.1, 7.23, 8.06, 8.64, 9.86, 10.3 μ. NMR: δ 5.96 (m, 2, OH), 5.62 (m, 2, 13 and 14-H), 5.37 (m, 2, 5 and 6-H), 2.57 (s, C≡CH), 1.10 (m, 11-methyl) ppm. Mass spectrum: M+ at m/e 374.2511 (theory 374.2455).

of unknown stereochemistry

Further elution with 17% ethyl acetate in hexane afforded 0.1 g. of 7-[2β-(3ξ-ethynyl-3ξ-hydroxy-trans-1-octenyl)-3α-methyl -5-oxo-1α-cyclopentyl]-cis-5-heptenoic acid as an oil, $\lambda_{max}^{film}$ 3.05, 3.4, 5.8, 6.83, 7.1, 7.23, 8.06, 8.63, 9.86, 10.3 μ. NMR: δ 6.38 (m, 2, OH), 5.71 (s, 2, 13 and 14-H), 5.41 (m, 2, 5 and 6-H), 2.48 (s, C≡CH), 1.13 (s, 11-methyl) ppm. Mass spectrum: M+ at m/e 374.2476 (theory 374.2455).

EXAMPLE 25

5β-Hydroxy-3α-Methyl-2β-(3-Oxo-Octyl)-1α-Cyclopentane Heptanoic Acid (9β-XXI)

A solution of 2.6 g. of 7-[5β-hydroxy-3α-methyl-2β-(3-oxo-trans-1-octenyl)-1α-cyclopentyl]-cis-5-heptenoic acid in 50 ml. of ethyl acetate was added to the prehydrogenated mixture of 0.70 g. of 10% Pd/C in 90 ml. of ethyl acetate and the mixture hydrogenated at 25° C. under atmospheric pressure until two equivalents of hydrogen were absorbed. After filtering, the solution was evaporated and the residue chromatographed on silica. Elution with 25% ethyl acetate in hexane afforded 2.2 g. of 5β-hydroxy-3α-methyl-2β-(3-oxo-octyl)-1α-cyclopentane heptanoic acid as an oil, $\lambda_{max}^{film}$ 3.0 (shoulder), 3.45, 5.82, 6.83, 7.08, 7.29 μ. NMR: δ 6.05 (s, 2, OH), 3.88 (m, 1, 9-H), 0.95 (d, J=5, 11-methyl) ppm. Mass spectrum: QM+ —H2O at m/e 337 (theory 337).

EXAMPLE 26

2β-[(3RS)-3-Ethynyl-3-Hydroxyoctyl]-5β-Hydroxy-3α-Methyl-1α-Cyclopentane Heptanoic Acid (9β-XXII)

A solution of 2.1 g. of 5β-hydroxy-3α-methyl-2β-(3-oxo-octyl)-1α-cyclopentane-heptanoic acid in 20 ml. of THF was added at 0° C. to ethynyl magnesium bromide (prepared from 40 ml. of 3M MeMgBr and excess acetylene) in 200 ml. of THF and stirred for 1 hour. The mixture was treated with aqueous ammonium chloride solution and extracted with ether. After washing with water and drying with magnesium sulfate, the extract was evaporated and the residue chromatographed on silica. Elution with 20% ethyl acetate in hexane afforded 1.91 g. of 2β[(3RS)-3-ethynyl-3-hydroxyoctyl]-5β-hydroxy-3α-methyl-1α-cyclopentane heptanoic acid, as an oil, $\lambda_{max}^{film}$ 3.05, 3.5, 5.85, 6.9, 8.1 (broad) μ. NMR: δ 5.25 (3, s, OH), 3.92 (m, 1, 9-H), 2.43 (s, 1, C≡CH), 0.98 (d, J=5.5, 11-methyl) ppm. Mass spectrum: QM+ —H2O at m/e 363 (theory 363).

EXAMPLE 27

2β-[(3RS)-3-Ethynyl-3-Hydroxyoctyl]-5-Oxo-3α-Methyl-1α-Cyclopentane Heptanoic Acid (XXIII)

An ice-cooled solution of 1.81 g. of 2β-[(3RS)-3-ethynyl-3-hydroxyoctyl]-5β-hydroxy-3α-methyl-1α-cyclopentane heptanoic acid in 190 ml. of acetone was treated with 8.5 ml. of 1.2M Jones reagent and stirred at 0° C. for three-fourth hours. The mixture was treated with 5 ml. of methanol and neutralized with aqueous sodium bicarbonate solution. After acidification with acetic acid, the mixture was extracted with ether and the extract was washed with water and dried with magnesium sulfate. Evaporation of the solvent and silica chromatography of the residue with 17% ethyl acetate in hexane afforded 0.9 g. of 2β-[(3RS)-3-ethynyl-3-hydroxyoctyl]-5-oxo-3α-methyl-1α-cyclopentane heptanoic acid as an oil, $\lambda_{max}^{film}$ 3.05, 3.45, 5.8, 6.83, 7.1, 7.23, 8.05, 8.6, 10.6 μ. NMR: δ 6.77 (m, 2, OH), 2.49 (s, C≡CH), 1.14 (d, J=5, 11-methyl) ppm. Mass spectrum: QM+ at m/e 379 (theory 379).

EXAMPLE 28

7-[3α-Methyl-5-Oxo-2β-(3-Oxo-Trans-1-Octenyl)-1α-Cyclopentyl]-Cis-5-Heptenoic Acid (XXIV)

An ice-cooled solution of 1.0 g. of 7-(2β-[(3S)-3-hydroxy-trans-1-octenyl]-3α-methyl-5-oxo-1α-cyclopentyl)-cis-5-heptenoic acid in 100 ml. of acetone was treated with 5 ml. of 1.2M Jones reagent and stirred at 0° C. for three-fourth hours. The mixture was treated with 5 ml. of methanol and neutralized with aqueous sodium bicarbonate solution. After acidification with acetic acid, the mixture was extracted with ether and the extract was washed with water and dried with magnesium sulfate. Evaporation of the solvent and silica chromatography of the residue with ethyl acetate/hexane affords 7-[3α-methyl-5-oxo-2β-(3oxo-trans-1-octenyl)-1α-cyclopentyl]-cis-5-heptenoic acid as an oil.

The subject matter which the applicants regard as their invention is particularly pointed out and distinctly claimed as follows:

1. A compound of the structure:

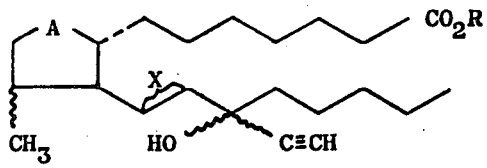

wherein A is CHOH or C=O; R is H or alkyl of from 1 to 6 carbon atoms, and
i. X is a single bond; or
ii. X is a trans double bond.

2. A compound of the structure:

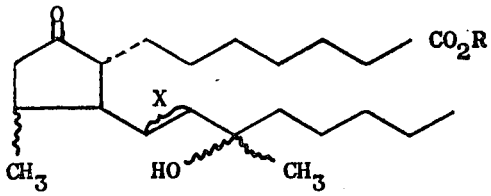

wherein R is H or alkyl of from 1 to 6 carbon atoms, and
i. X is a single bond; or
ii. X is a trans double bond.

3. A compound of the structure:

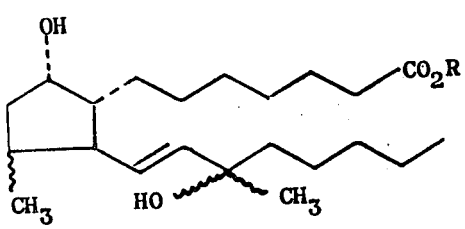

wherein R is H or alkyl of from 1 to 6 carbon atoms.

4. A compound of the structure:

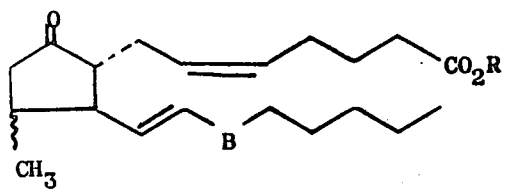

wherein B is C(CH₃)OH or C(C≡CH)OH, and R is H or alkyl of from 1 to 6 carbon atoms.

5. A compound of the structure:

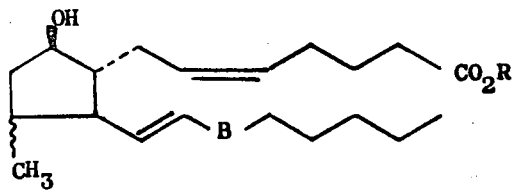

wherein B is C(CH₃)OH, or C(C≡CH)OH; and R is H, or alkyl of from 1 to 6 carbon atoms.

6. A compound of the structure:

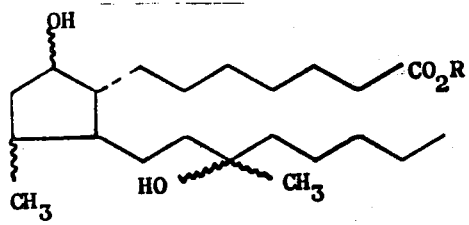

wherein R is H or alkyl of from 1 to 6 carbon atoms.

7. A compound of the structure:

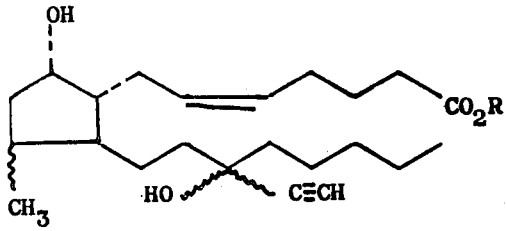

wherein R is H, or alkyl of from 1 to 6 carbon atoms.

8. A compound of the structure:

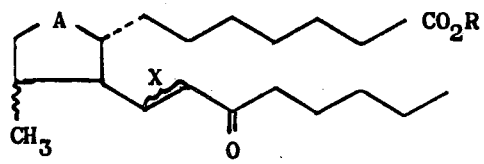

wherein A is CHOH or C=O; R is H or alkyl of from 1 to 6 carbon atoms, and
 i. X is a single bond; or
 ii. X is a trans double bond.

9. A compound of the structure:

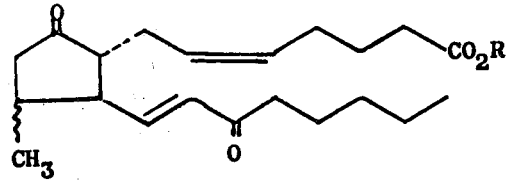

wherein R is H or alkyl of from 1 to 6 carbon atoms.

10. A compound of the structure:

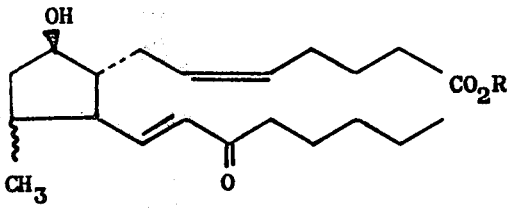

wherein R is H or alkyl of from 1 to 6 carbon atoms.

11. A compound of the structure:

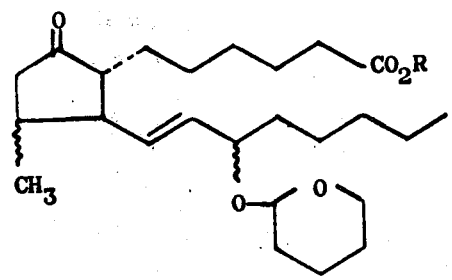

wherein R is H or alkyl of from 1 to 6 carbon atoms.

12. A compound of the structure:

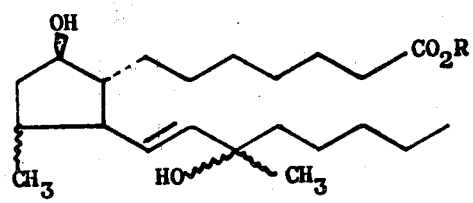

wherein R is H or alkyl of from 1 to 6 carbon atoms.

* * * * *